United States Patent [19]
Stark et al.

[11] Patent Number: 6,127,176
[45] Date of Patent: Oct. 3, 2000

[54] MUTANT CELL LINES UNRESPONSIVE TO INTERLEUKIN 1

[75] Inventors: George R. Stark, Shaker Heights; Xiaoxia Li, Solon, both of Ohio

[73] Assignee: Cleveland Clinic Foundation, Cleveland, Ohio

[21] Appl. No.: 09/095,485

[22] Filed: Jun. 10, 1998

[51] Int. Cl.$^7$ .............................. C12N 5/10; C12N 5/16; C12N 5/22
[52] U.S. Cl. ........................ 435/325; 435/366; 435/369; 435/252.3
[58] Field of Search .................................. 435/369, 368, 435/252.3, 325

[56] References Cited

PUBLICATIONS

Altmeyer et al. Cellular Immunology, vol. 138(1), pp. 94–107, Oct. 1991.

"Jak–STAT Pathways and Transcriptional Activation in Response to IFNs and Other Extracellular Signaling Proteins" by Darnell, et al., *Scientce,* vol. 264, Jun. 3, 1994, pp. 1415–1421.

"Use of a Selectable Marker Regulated by Alpha Interferon To Obtain Mutations in the Signaling Pathway" by Pelligrini, et al., *Molecular and Cellular Biology,* vol. 9, No. 11, Nov. 1989, pp. 4605–4612.

"RIP mediates tumor necrosis factor receptor 1 activation of NF–κB but not Fas/APO–1 initiated apoptosis" by Ting, et al., *The EMBO Journal,* vol. 15, No. 22, 1996, pp. 6189–6196.

"Early Lethality, Functional NF–κB Activation, and Increased Sensitivity to TNF–Inducesd Cell Death in TRAF2–Deficient Mice" by Yeh, et al., *Immunity,* vol. 7, Nov. 1997, pp. 715–725.

MyD88: An Adapter That Recruits IRAK to the IL–1 Receptor Complex by Wesche, et al., *Immunity,* vol. 7, Dec. 1997, pp. 837–847.

"A cytokine–responsive IκB kinase that activates the transcription factor NF–κB" by DiDonato, et al., *Nature,* vol. 388/7, Aug. 1997, pp. 548–554.

"Identification and Characterization of an IκB Kinase" by Regnier, et al., *Cell,* vol. 90, Jul. 25, 1997, pp. 373–383.

"Complementation Cloning of NEMO, a Component of the IκB Kinase Complex Essential for NF–κB Activation" by Yamaoka, et al., *Cell,* vol. 93, Jun. 26, 1998, pp. 1231–1240.

"IRAK: A Kinase Associated with the Interleukin–1 Receptor" by Cao, et al., *Science,* vol. 271, Feb. 23, 1996, pp. 1128–1131.

*Primary Examiner*—Prema Mertz
*Assistant Examiner*—Fozia Hamud
*Attorney, Agent, or Firm*—Calfee, Halter & Griswold LLP

[57] ABSTRACT

Mutant cell lines which have lost their ability to respond to IL-1 are provided. In one embodiment, the mutant cell line lacks or is essentially free of IL-1 receptor associate kinase (IRAK), an IL-1 signaling pathway component. The present invention also provides a method for making mutant cell lines that are unresponsive to IL-1, TNF, or to both cytokines. The method comprises the steps of: transfecting cells with a Herpes Simplex Virus thymidine kinase (HSV-TK) gene and a second gene for positive selection, each of said genes being operatively linked to an IL-1 inducible promoter or a TNF inducible promoter; selecting for transfected cells that express HSV thymidine kinase and the product of the positive selection gene in response to IL-1 or TNF; determining a gancyclovir concentration which kills the selected cells in the presence of IL-1 or TNF and which does not kill the selected cells in the absence of IL-1 or TNF; mutagenizing the selected cells using a chemical mutagenizing agent; and treating the mutagenized cells with the determined concentration of gancyclovir and IL-1 or TNF. The present invention also relates to a method of identifying domains or amino acids in IRAK that are essential for IRAK to function in the IL-1 signaling pathway.

9 Claims, 5 Drawing Sheets

Fig. 2

```
       -740                -720                -700                -680
GCCTGCCTCGGCCTCCCAAAGTGGTGGGATTACAGGCGTGAGCCACTGTGCCTGGCCTCC

-660                -640                -620
TTTTTATTTTTTTCACTGAACAAACCATGAAACTTTCCCAGATGTAAATATCTATTTCCC

-600                -580                -560
ATTTTTCTTTTTTTAAAATAAGGCATTATTTTAACCATTTGAGTGTTAGATATTATTTTT

-540                -520                -500
AGATAATATTTTAATTTAGCATAACTGCCGTGCAAAATCTGAAGATTAATATCTACCTTG

-480                -460
TGAGTCATTCCTCTGTGAGACAGTGCATGTTAAATATGTTGAATTGGCAGGTGAAAAAGG

-440                -420                -400                -380
AAGAAAAAATGAGTAGTGATTGGTTATCCACAGCTATGAATGAGAAATTGAAGGTAGTAG

-360                -340                -320
ACTATGGATGACAAACCTATTCTTGGTTTCCTTCTGTTTCTGAAATTCTAATTACTACCA

-300                -280                -260
CAACTACATGAGAGACACTACTAACAAGCAAAGTTTTACAACTTTTTAAAGACATAGACT

PALINDROMIC SEQUENCE
                  -240         |        -220                -200
TTATGTTATTATAATTAAAA|ATCATGCATTTTTGTCATATTAATAAAA|TTGCATATACGA

ATF site
                  -180                -160               |
TATAAAGGCATGGACAAAGGTGAAGTAGCTTCAAGAGACAGAGTTTC|TGACATCA|TTGTA NFkB site 1      NFkB site 2           NFkB site 3
     -140          |-120           |        -100          |        -80
ATTTTAAGCATCGT|GGATATTCCC| |GGGAAAGGTTT|TTGGATGCCATT|GGGGATTTCC|TCT
```

Fig. 2 (con't)

Elam-1 Promoter

Isolation of IL-1 Unresponsive Mutants

MUTANT CELL LINES UNRESPONSIVE TO INTERLEUKIN 1

This invention was made a part with government support under Grant Number PO1-CA62220 from the National Institutes of Health. The government has certain rights in this invention.

BACKGROUND OF THE INVENTION

Interleukin 1 (IL-1) is a pro-inflammatory cytokine produced mainly by macrophages and monocytes in response to inflammation, infection, and other environmental challenges. At low concentrations, IL-1 functions as a mediator of local inflammation. At higher concentrations, IL-1 enters the blood stream. Systemic IL-1 has the ability to cause fever, to induce synthesis of acute phase plasma proteins by the liver, and to initiate metabolic wasting. Accordingly, it is desirable to have inhibitors that block IL-1 mediated inflammation. Similarly, it is desirable to have inhibitors that block the inflammation induced by tumor-necrosis factor (TNF), a cytokine having functions similar to that of IL-1.

IL-1 elicits most of its biological effects by activating transcription factors such as nuclear factor kappa B (NFκB), activating transcription factor (ATF) and activator protein (AP1) and thereby inducing the transcription of various genes. The first step in the IL-1 transcription signaling pathway involves binding of IL-1 to a receptor on a target cell. The final step in the IL-1 signaling pathway presumably involves interaction between the transcription activators NFκB, ATF or AP1 with their respective response elements in the promoters of an IL-1 inducible gene.

A proposed model for the major IL-1 initiated and the TNF-initiated signaling pathways is shown in FIG. 1. Since genetic information about the components of these pathways is largely lacking, it is uncertain if these proposed signaling pathways are complete or whether the proposed order of steps is entirely correct.

Accordingly, it is desirable to have model systems for obtaining genetic information about the IL-1 and TNF signaling pathways. Specifically, it is desirable to have mutant cell lines which, in contrast to their parent cell lines, are unresponsive to IL-1 or TNF. Such mutant cell lines are useful model systems for testing the accuracy of the currently proposed IL-1 and TNF signaling pathways. Such mutant cell lines also allow one to determine whether there are other, as yet unidentified, components in the proposed pathways. Mutant cells that lack a known component of one or more of the proposed pathways are especially desirable. Such cell lines are useful model systems for identifying the regions of the known protein that are essential for the known protein to function as an IL-1 or TNF signaling pathway component. Such information allows one to design molecules which interact with these essential regions and which may be useful for blocking the biological effects of IL-1 and TNF.

SUMMARY OF THE INVENTION

The present invention provides mutant cell lines which have lost their ability to respond to IL-1. In one embodiment, the mutant cell line lacks or is essentially free of IL-1 receptor associate kinase (IRAK), an IL-1 signaling pathway component. Such cell line is a useful model system for identifying target sites for inhibitors of IRAK.

The present invention also provides a method for making mutant cell lines that are unresponsive to IL-1, TNF, or to both cytokines. The method comprises the steps of: transfecting cells with a Herpes Simplex Virus thymidine kinase (HSV-TK) gene and a second gene for positive selection, each of said genes being operatively linked to an IL-1 inducible promoter or a TNF inducible promoter; selecting for transfected cells that express HSV thymidine kinase and the product of the positive selection gene in response to IL-1 or TNF; determining a gancyclovir concentration which kills the selected cells in the presence of IL-1 or TNF and which does not kill the selected cells in the absence of IL-1 or TNF; mutagenizing the selected cells using a chemical mutagenizing agent; and treating the mutagenized cells with the determined concentration of gancyclovir and IL-1 or TNF. The present invention also relates to cells made by such method.

The present invention also relates to a method of identifying domains or amino acids in IRAK that are essential for IRAK to function in the IL-1 signaling pathway.

BRIEF DESCRIPTION OF THE FIGURES

FIG. 2 also depicts the location of the NFκB response element and the ATF response element.

DETAILED DESCRIPTION OF THE INVENTION

In accordance with the present invention, a method for making mutant mammalian cell lines, preferably human cell lines, that are unresponsive to stimulation by IL-1, or TNF, or to both cytokines, is provided. In the first step of the method cells, preferably human cells, are co-transfected with DNA molecules comprising the Herpes Simplex Virus thymidine kinase (HSV-TK) gene, hereinafter referred to as the "negative selection gene", and with DNA molecules comprising a gene whose product confers resistance to a positive selection marker, hereinafter referred to as the "positive selection gene". Examples of positive selection genes include drug resistance genes, such as the neomycin resistance gene, the puromycin resistance gene, the hygromycin resistance gene, and the zeocin resistance gene.

Figure 1:
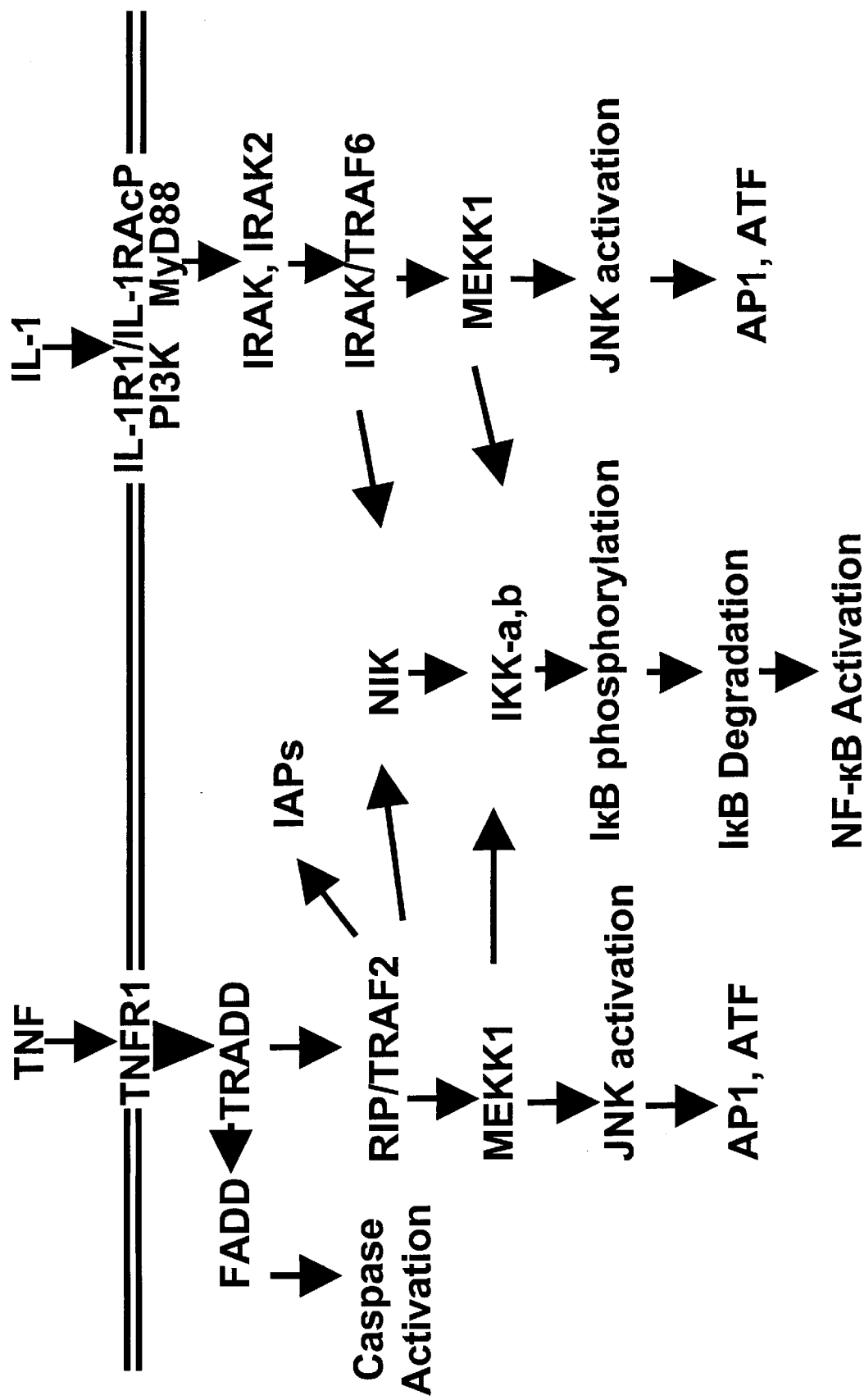
FIG. 1 is a model for the NFκB signal transduction pathways and the ATF/AP1 signal transduction pathways initiated by TNF and IL-1.
Figure 2:
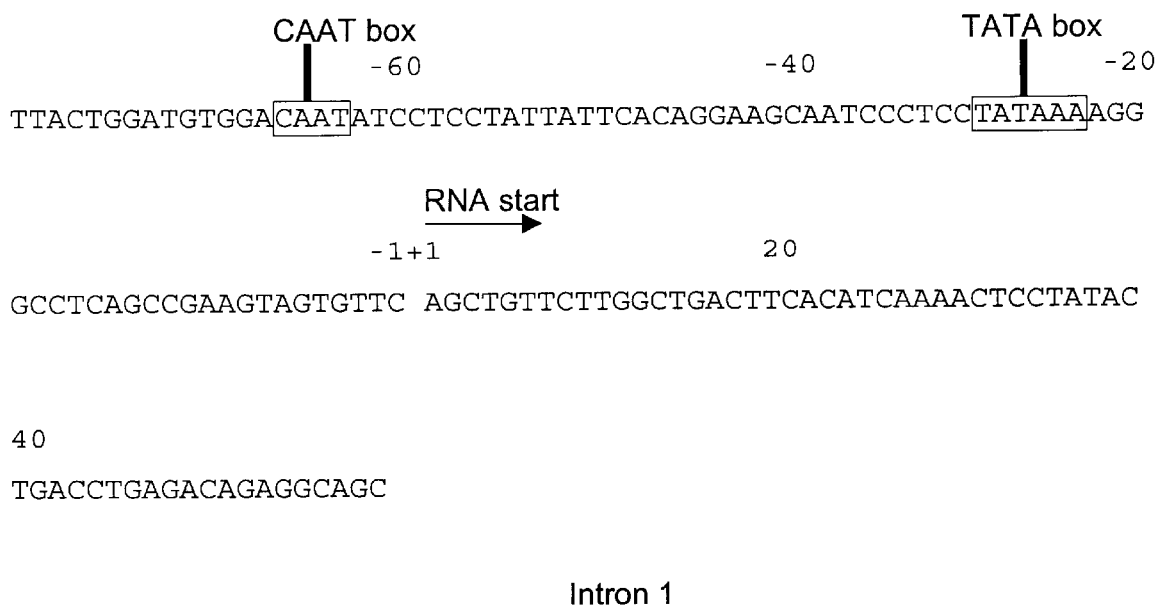
FIG. 2 is the nucleotide sequence, SEQ ID NO: 1, of an upstream fragment of the Elam gene extending from nucleotide −730 to nucleotide +53.

The HSV-TK gene and the positive selection gene are both operatively linked to an IL-1 inducible promoter, a TNF-inducible promoter, or to a promoter comprising elements that are responsive to transcription factors which are activated by both IL-1 and TNF. Typically, IL-1 inducible promoters and the TNF inducible promoters contain a binding site for NFκB, ATF, or AP-1. The consensus sequence of the binding sites for NFκB is GGGGACTTTCCC, SEQ ID NO:2; for ATF is TGACCTCA; and for AP-1 is TGACTCA. The nucleotide sequence of the promoter for the Elam gene, a gene that is responsive to stimulation by both IL-1 and TNF is shown in FIG. 1 and Whelan et al (1991) Nucleic Acid Research, Vol. 19, 2645–2649. The nucleotide sequence of the promoter for the IL-8 gene, another gene responsive to stimulation by IL-1 and TNF, is shown in Mukaida et al (1990) J. Biol. Chem. 265: 21128–33.

To allow for testing of more than one pathway, it is preferred that the IL-1 inducible promoter or the TNF-inducible promoter contains binding sites, i.e., response elements, for NFκB and for either AP1 or ATF. The DNA comprising the HSV-TK gene and the DNA comprising the positive selection gene may be on the same DNA molecule or, preferably, on separate DNA molecules. The cells are co-transfected using conventional procedures such as, for example, calcium phosphate precipitation of plasmids comprising cDNAs of the HSV-TK gene and the positive selection gene. Alternatively, the cells may be co-transfected with DNA molecules comprising the HSV-TK gene and the positive selection gene by DEAE-dextran mediated transfection, cationic lipid-mediated transfection, or electroporation. Such techniques are known in the art.

Thereafter, representative colonies derived from individual transfected cells are separately cultured in medium containing one of the following: gancyclovir (GCV); GCV plus IL-1 or TNF; the positive selection marker, e.g., the antibiotic to which the product of the positive selection gene confers resistance, or the positive selection marker plus IL-1 or TNF. Such procedure allows one to identify cell lines expressing HSV thymidine kinase and the product of the positive selection gene. Transfected cells that survive in medium containing GCV and in medium containing IL-1 or TNF and the positive selection marker and that die in medium containing the positive selection marker or in medium containing IL-1 or TNF and GCV are selected and expanded into stably-transfected cell lines using conventional techniques.

Representative samples of the stably-transfected cell lines are cultured in medium containing IL-1 or TNF and varying concentrations of GCV and in medium containing varying concentrations of GCV but lacking the cytokine. Such analysis permits determination of a GCV concentration, hereinafter referred to as the "predetermined GCV concentration", which allows growth of cells expressing significant basal levels of HSV-TK but which kills cells that express high levels of HSV-TK in response to treatment with IL-1 or TNF.

Cells from one or more of the stably-transfected cell lines are mutagenized by treatment with a chemical mutagenizing agent, preferably a mutagenizing agent that causes frame-shift mutations in DNA. Suitable mutagenizing agents include, for example, intercalating agents such at ICR 191. Thereafter, the mutagenized cells are selected using medium containing IL-1 or TNF and the predetermined concentration of GCV to provide a mutant cell line that is unresponsive to IL-1, or TNF, or to both cytokines.

The present method permits preparation of cell lines that are unresponsive to IL-1 or TNF using any mammalian cell line that is responsive to IL-1 or TNF. The present method allows one to obtain mutant cell lines that are unresponsive to IL-1, or TNF by mutagenizing transfected cells that express significant basal levels of thymidine kinase as well as by mutagenizing transfected cell lines that express little or no thymidine kinase. Thus, in the present method for preparing IL-1 and TNF unresponsive cell lines, one can employ any IL-1 or TNF inducible promoter, even those with basal activity, to drive expression of the HSV-TK gene.

The present invention also provides mutant cells or cell lines which are unresponsive to IL-1, or TNF, or both. Preferably, the mutants cells comprise within the genome thereof an HSV-TK gene operatively linked to an IL-1 inducible promoter. More preferably, the mutant cells further comprise, within the genome thereof, a positive selection gene operatively linked to an IL-1 inducible promoter. Such mutant cell lines are useful for testing the accuracy of the currently proposed IL-1 and TNF signaling pathways. Such mutant cell lines, particularly those that contain an IL1 or TNF inducible promoter comprising response elements for NFκB and ATF or AP1, also permit identification of components that are members of more than one branch of the IL-1 and/or TNF signaling pathways. Such cell lines also allow identification of new components of the IL-1 and TNF signaling pathways.

In one embodiment the mutant cells lack or are essentially free of the IL-1 signaling component IRAK. A mutant cell is considered to be essentially free of IRAK when IRAK cannot be detected in the cell using an immunoassay which employs IRAK-specific antibodies. Preferably, such mutant cells comprise the following components of the IL-1 inducible, NFκB-meditated pathway: an IL-1 receptor, the IL-1 receptor accessory protein (IL-RAcP), myeloid differentiation marker 88 (MyD88), IRAK2, TNF-receptor associated factor 6 (TRAF6), NFκB-inducing kinase (NIK), the conserved helix-loop helix ubiquitous kinase (CHUK) (shown as IKK1 in FIG. 1), and NFκB. A mutant cell line unresponsive to IL-1, lacking IRAK, and comprising the known components in the IL-1 inducible, NFκB-mediated signaling pathway was deposited with the American Type Culture Collection (ATCC), 10801 University Boulevard Manassas, Va. 21110-2209 U.S.A., on Jun. 11, 1998. Such mutant cell line has the ATCC Accession Number ATCC CRL-12540. The ATCC is a recognized depository of the Budapest Treaty.

The present invention also provides a method for identifying domains or amino acids in IRAK that are essential for IRAK to function in the IL-1 signaling pathway. The method comprises the steps of providing a mutant cell which is unresponsive to IL-1 and lacks IRAK; transfecting the mutant cell with DNA comprising a modified gene encoding a IRAK having a mutation in the amino acid sequence thereof, and assaying for restoration of the IL-1 signaling pathway in the transfected, mutant cell. Restoration of the signaling pathway indicates that the mutation does not disrupt the ability of the mutated IRAK to function in the IL-1 signaling pathway. Failure to restore the pathway indicates that the domain or amino acid which has been mutated or modified is essential for IRAK to function in the IL-1 signaling pathway. Preferably, the mutant cell comprises the remaining components of the IL-1 signaling pathway.

For ease in assaying restoration of the IL-1 signaling pathway, it is preferred that the mutant cell also comprise a positive selection gene operatively linked to an IL-1 inducible promoter, or a negative selection gene operatively linked to an IL-1 inducible promoter, or a reporter gene operatively linked to an IL-1 inducible promoter or combinations thereof. Examples of reporter genes are the luciferase gene and the β-galactosidase gene. By way of example, a mutant cell containing a negative selection gene, such as for example an HSV-TK gene, can be assayed by transfecting the mutant cell with the modified IRAK gene, exposing the transfected mutant cell to negative selection, and assaying for the ability of the transfected mutant cell line to survive in medium containing the corresponding negative selection agent. Preferably, the IL-1 inducible promoter comprises more than one response element to allow for assaying of more than one IL-1 signaling pathway.

Modified IRAK genes encoding a mutated IRAK protein, i.e., an IRAK protein having an amino acid sequence different from the wild-type sequence are made through conventional methods, such as, for example, polymerase chain reaction ("PCR") based site-directed mutagenesis. Such technique allows for deleting amino acids from the wild-type sequence, adding amino acids to the wild-type sequence, or substituting for amino acids in the wild-type sequence. In PCR based site-directed mutagenesis a DNA molecule encoding a wild-type IRAK amino acid sequence is ligated into a cloning vector and used as a template. Vector-specific primers and oligonucleotide primers designed to encode the changes, i.e., the deletions, additions, or substitutions, sought to be introduced into the gene are used during amplification to provide DNA molecules containing the desired modified gene. DNA molecules containing the modified IRAK gene are isolated from the PCR products using conventional methods and transfected into the mutant cell line using conventional techniques.

Identifying domains or amino acids in IRAK that are essential for IRAK to function in the IL-1 signaling pathways allows one to design biochemicals that are targeted at, i.e., interact with, the essential amino acid or block the function of, the essential domain. Such biochemicals have the potential of blocking the IL-1 signaling pathway and preventing IL-1 induced inflammation.

The following non-limiting examples are presented to further illustrate the present invention.

EXAMPLE 1

Making Mutant Cell Lines that are Unresponsive to Interleukin 1

A. Transfection

Figure 3:
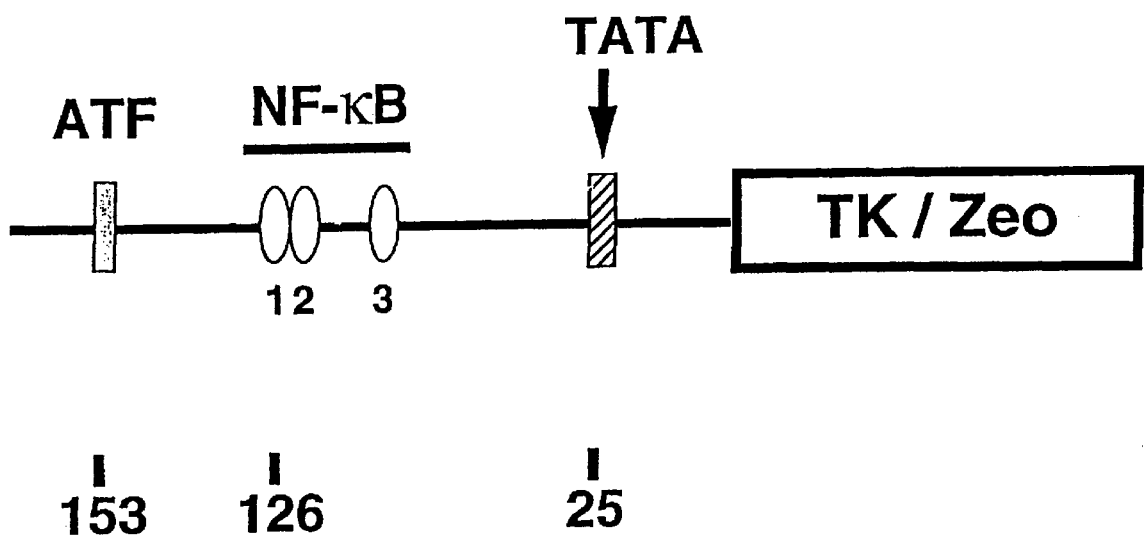
FIG. 3 is a schematic representation of the Elam-1 promoter linked to a Herpes Simplex Virus thymidine kinase gene or a zeocin resistance gene.
Figure 4:
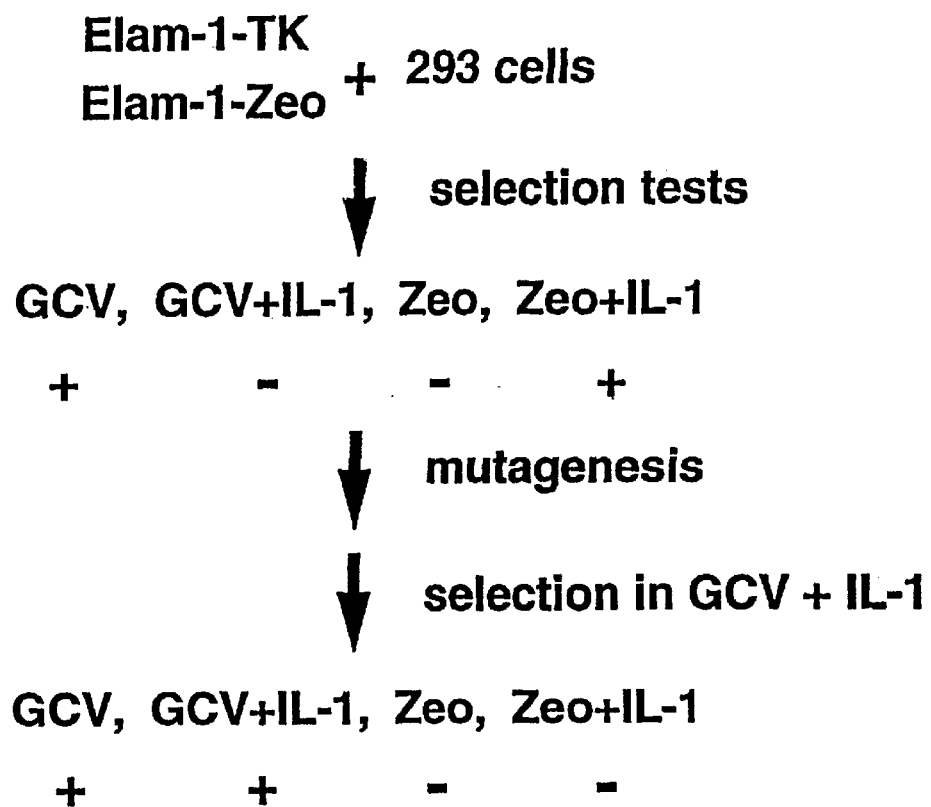
FIG. 4 is a schematic representation of a method used to produce mutant cell lines which are unresponsive to IL-1.

Human embryonic kidney 293 cells ("293 cells") obtained from Tularik, South San Francisco, Calif., and plasmids pELAM-TK and plasmid pELAM-Zeo were used to make mutant cell lines that are unresponsive to IL-1. The 293 cells contain a transfected IL-1 receptor to enhance response of the cells to stimulation by IL-1. The 293 cells were maintained in Dulbecco's modified Eagle's Medium (DMEM) supplemented with 10% fetal calf serum, 100 $\mu$g/ml penicillin G, and 100 $\mu$g/ml streptomycin.

pELAM-TK comprises a cDNA of the HSV-TK gene, as described in Askew et al. 1993 Mol. Cell. Biol. 13, 4115–4124. The HSV-TK gene is operatively linked to the IL-1 inducible promoter of the Elam-1 gene. The Elam-1 gene is responsive to both IL-1 and TNF. The IL-1 inducible promoter contains the response elements shown in FIG. 3. pELAM-TK was made by cloning an upstream fragment of the Elam 1 gene, as shown in FIG. 1, and the cDNA of the HSV thymidine kinase gene into pGL3-Basic from Promega. The Elam-1 gene fragment is cloned into the plasmid directly upstream of the thymidine kinase gene.

pELAM-Zeo comprises the zeocin resistance gene operatively linked to the Elam-1 promoter. pELAM-Zeo was made by cloning the upstream fragment of Elam-1 gene shown in FIG. 1 directly upstream of the zeocin resistance gene (Invitrogen).

The 293 cells were cotransfected by a calcium phosphate precipitation method using 10 $\mu$g of each plasmid. Recombinant transfected cell lines that comprise both genes and that express both genes in response to treatment with IL-1 were selected by assaying for transfected cells that survive in GCV (5 $\mu$g/ml), die in GCV+IL-1 (10 ng/ml), die in Zeo (500 $\mu$g/ml) and survive in Zeo+IL-1 (10 ng/ml). Recombinant human IL-1 was obtained from the National Cancer Institute, Frederick, Md. GCV was obtained from the Cleveland Clinic Foundation, Cleveland Ohio, and zeocin was obtained from Invitrogen, Carlsbad, Calif. One of the selected cell lines was named 293-Zeo/TK.

B. Determining the GCV Concentration for Selecting Mutant Cell Lines

The concentration of GCV which killed the transfected cells in the presence of IL-1 and which did not kill the cells in the absence of I IL-1, i.e., the predetermined GCV concentration, was determined empirically. The predetermined GCV concentration was obtained for each transfected cell line by titration, i.e. by culturing cells from each transfected cell line in medium containing 10 ng/ml of IL-1 and different concentrations of GCV and in medium lacking IL-1 and containing the same concentrations of GCV. Depending on the cell line tested, the concentration of GCV which achieved the desired result, i.e. the predetermined GCV concentration, varied from about 0.1 $\mu$g/ml to about 10 $\mu$g/ml. For the transfected cell line named 293-Zeo/TK, the predetermined GCV concentration was 5 $\mu$g/ml. The results showed that 293-Zeo/Tk cells were completely killed when cultured in 5 $\mu$g/ml GCV and 10 ng/ml IL-1, while 293-Zeo/Tk cells survived quite well when cultured in medium containing 5 $\mu$g/ml GCV and lacking IL-1.

C. Mutagenesis

The stably transfected 293-TK/Zeo cells were expanded and divided into multiple cell pools, with $10^7$ cells per pool. Cells from each pool were cultured for three hours in medium containing from 1–5 $\mu$g/ml of the intercalating agent ICR191, which was obtained from ICN Biochemicals, Inc., Cleveland, Ohio. The concentration of ICR191 used was determined empirically by assaying for a concentration that kills 50–70% of the cells in the pool. Cells were then rinsed twice in serum free medium and cultured in complete medium lacking ICR191for recovery. After the recovery, cells were subjected to an additional 4 rounds of mutagenesis.

D. Selection

To isolate IL-1 unresponsive mutants, representative samples of mutagenized cells from each pool were selected in medium containing 5 $\mu$g/ml GCV and 10 ng/ml IL-1. Fresh GCV and IL-1 were added to these cells every three days for approximately 2 to 3 weeks. Surviving colonies or cell lines were picked and expanded in nonselection medium. These colonies were then subjected to drug selection tests to characterize the selected cell lines. The drug selection tests involved culturing the cell lines in medium containing one of the following: 5 $\mu$g/ml GCV, 5 $\mu$g/ml GCV+10 ng/ml IL-1, 500 $\mu$g/ml Zeo, 500 $\mu$g/ml Zeo+10 ng/ml IL-1. Over 90% of the cell lines survived in GCV or GCV+IL-1 and died in Zeo or Zeo+IL-1.

Since the Elam-1 promoter contains NFκB binding sites, the mutant cell lines were further screened for their loss of NFκB activation upon stimulation with IL-1 or TNF. NFκB activation was determined by a gel shift assay using the NFκB binding site (5'-GAGCAGAGGGAAATTCCGTAACTT-3', SEQ ID NO:3) from the IP10 gene as a probe. About 10–30% of the cell lines from the selection had lost the NFκB activation upon stimulation with either IL-1 or both IL-1 and TNF. Four mutant cell lines, including one named I1A, from four independent mutagenized pools were derived from this screen. IL-1 induced NFκB activation was greatly reduced in each of these mutant cell lines.

An Elam-1 promoter driven luciferase plasmid, obtained from Tularik, was transfected into cells from each of the four mutant cell lines and into cells from the 293-TK/Zeo cell line. Luciferase activity in the transfected cells was determined with Luciferase Assay System from Promega. Both IL-1 and TNF upregulated the Elam-1 promoter driven luciferace activity in wild type cells (293-TK/Zeo).

However, IL-1 induced promoter activity was completed abolished in the four mutant cell lines, while their TNF response was intact. These results indicate that the four mutant cell lines have a defect in a component that is specific to the IL-1 signaling pathway.

Expression of the endogenous IL-1 and TNF responsive gene IL-8 was assayed in a northern analysis. The sequence of the IL-8 gene is provided in Mukaida et al, J. Biol. Chem. 265: 21128–33, 1990. IL-8 gene expression was induced by both IL-1 and TNF in wild type 293-TK/Zeo cells. TNF also induce expression of the IL-8 gene in cells from the mutant cell line. In contrast, IL-1 induced IL-8 gene expression was greatly reduced in the isolated mutant cell lines.

To assign the mutant cell lines to complementation groups, a puromycin resistant population from each mutant cell line was fused to a hygromycin-resistant population from each of the four mutants. IL-1 induced NFκB activation was then examined in each hybrid population. This analysis showed that two of the mutant cell lines are in the same complementation group and that one of the other mutant cell lines belongs to another complementation group. The I1A cell line comprises a third complementation group.

EXAMPLE 2

Mutant Cell Lines Lacking IRAK

The mutant cell line, I1A, which was made as described above in example 1, was deposited with the ATCC on Jun. 11, 1998 and assigned Accession Number ATCC-CRL-12450.

Western blot analyses were performed on cells from mutant cell line I1A using antibodies against I1-R1, I1-1RAcP, Myd88, TRAF6, NIK, CHUK, IRAK and IRAK2. All antibodies were obtained from Tularik. Western blot analysis indicated that I1A cells lack IRAK, which is a serine-threonine kinase recruited to the IL-1 receptor complex upon IL-1 stimulation. This result was confirmed by northern blot analysis using IRAK cDNA as a probe. Northern blot analysis indicated that IRAK mRNA was also lacking in the I1A cells. Western blot analyses indicated that I1A cells contain the following components of the IL-1 signaling pathway: I1-R1, I1-1RAcP, Myd88, TRAF6, NIK, CHUK, and IRAK2.

To test whether IRAK can complement the defect in mutant I1A cells, a thymidine kinase promoter driven IRAK gene, obtained from Tularik, was transfected back into I1A cells. The resulting cells, named I1a-IRAK, exhibited the same phenotype as wild type 293-TK/Zeo cells in drug selection tests. The I1A-IRAK cells survived in 500 μg/ml Zeo+10 ng/ml IL-1, died in 500 μg/ml Zeo, died in 5 μg/ml GCV+10 ng/ml IL-1 and survived in 5 μg/ml GCV. Luciferase reporter assay showed that IL-1-induced Elam-1 promoter driven luciferase activity was restored in I1A-IRAK cells. Furthermore, IL-1-induced activation of NFκB was also restored in I1A-IRAK cells. These results indicate that IRAK complements the defect in I1A mutant cells.

EXAMPLE 3

Using I1A Mutant Cells to Assess Involvement of IRAK in IL-1 Induced Jun Kinase Activation To determine whether IRAK is a component of the IL-1-induced Jun kinase pathway, a Jun kinase assay was performed in both wild type cells and I1A cells. 2 μg of GST-Jun was included in the kinase reaction which was performed in 50 μl kinase buffer containing 20 mM Hepes, pH7.0, 20 mM MgCl$_2$, 1 mM ATP, 10 μci of [γ-$^{32}$P]ATP at 30° C. for 30 min. Samples were then analyzed by 10% SDS-PAGE and autoradiography.

Both IL-1 and UV treatment activated Jun kinase in wild type cells (293-TK/Zeo). However, IL-1 induced Jun kinase activation was abolished in I1a cells, while UV treatment activated Jun kinase in the mutant I1A cells. In I1A cells stably transfected with IRAK, IL-1 induced activation of Jun kinase was restored. These results show that IRAK is a necessary component of the IL-1 induced Jun kinase activation pathway.

EXAMPLE 4

Using I1A Mutant Cells to Characterize the Order of Steps in the IL-1 Signaling Pathway Previous studies have shown that ectopic expression of MyD88 induces NFκB activation. To determine whether MyD88 is a component of the IL-1 signaling pathway, a plasmid comprising MyD88 driven by the CMV promoter was cotransfected with pElam-luc into the wild cells (293-TK/Zeo) and into I1A cells that lack IRAK. The MyD88 plasmid was obtained from Tularik. Luciferase activity in the MyD88-transfected, 293-TK/Zeo cells was dramatically increased as compared to cells transfected with pElam-luc alone. However, the effect of MyD88 on the Elam-1 promoter was not observed when MyD88 and pElam-luc were cotransfected into cells that lack IRAK. In I1A cells stably transfected with IRAK, the effect of MyD88 on the Elam-1 promoter was restored. This result suggests that IRAK is required for the function of MyD88, probably as a downstream effector of MyD88.

To determine whether IRAK functions upstream or downstream of TRAF6 in the IL-1 signaling pathway, wild-type (293-TK/Zeo) and I1A cells were cotransfected with pElam-luc and an expression vector comprising the gene for TRAF6 driven by the CMV promoter. Elam promoter driven-luciferase activity was increased in both cell lines as compared with cells transfected with Elam-luc alone. This result shows that TRAF6 can still function by interacting with the downstream components of the signaling pathway in the absence of IRAK, confirming that TRAF6 functions downstream of IRAK. Taken together, the above results indicate that IRAK functions between MyD88 and TRAF6 in the IL-1 signaling pathway.

EXAMPLE 5

Using I1A Mutant Cells to Asses the Ability of a Mutated IRAK to Function in the IL-1 Signaling Pathway To examine whether the kinase activity of IRAK is required for its function in IL-1 signaling, the ATP binding site of IRAK was abolished by changing the lysine at amino acid 239 to alanine (K239A). The TK promoter driven IRAK-K239A was transfected into I1A (I1A-IRAK-K239A). The K239A mutation completely abolished the kinase activity of IRAK. Surprisingly, IRAK-K239A functioned quite similarly to wild-type IRAK. First, I1A-IRAK-K239A cells exhibited the same phenotype as I1A-IRAK cells in drug selection tests. The I1A-IRAK cells and the I1A-IRAK-K239A cells both survived in Zeo+IL-1, died in Zeo, died in GCV+IL-1 and survived in GCV. Luciferase reporter assay showed that IL-1-induced Elam-1 promoter activity was also restored in I1A-IRAK-K239A cells.

Furthermore, the K239A mutation in IRAK did not block the ability of the mutated protein to mediate activation of NFκB in response to stimulation of the I1A-IRAK-K239A cells with IL-1. Similarly, the K239A mutation in IRAK did not block the ability of the mutated protein to mediate activation of Jun kinase activation in response to stimulation of the I1A-IRAK-K239A cells with IL-1. The constitutive activation of Elam-Luc by MyD88 was also restored in I1A-IRAK-K239A cells, suggesting the kinase activity of IRAK is not required for its recruitment to the receptor complex.

---

What is claimed is:

1. A mutant cell that lacks IL-1 receptor associated kinase and comprises an HSV thymidine kinase gene operatively linked to an IL-1 promoter and a zeomycin resistance gene operatively linked to an IL-1 promoter, wherein said mutant cell is a member of cell line I1A, ATCC Accession Number CRL-12450.

2. A method of making a mutant mammalian cell that lacks a functional component of the IL-1 signaling pathway, the TNF signaling pathway, or both the IL-1 and the TNF signaling pathways, said method comprising the following steps:

(a) transfecting mammalian cells which are responsive to IL-1 or TNF with a first gene and a second gene, said first gene being an HSV thymidine kinase gene; said second gene being a positive selection gene, wherein said first gene and said second gene are operatively linked with an IL-1 or a TNF inducible promoter;

(b) selecting for transfected cells that express HSV thymidine kinase and the product of the positive selection gene in response to IL-1 or TNF;

(c) determining a gancyclovir concentration which kills the transfected cells of step (b) in the presence of IL-1 or TNF and which does not kill said transfected cells in the absence of IL-1 or TNF;

(d) mutagenizing said transfected cells using a chemical mutagenizing agent;

(e) treating said mutagenized, transfected cells with said concentration of gancyclovir and IL-1 or TNF to provide mutant cells unresponsive to said cytokine;

wherein said mutant cells lack a functional component of the IL-1 signaling pathway, the TNF signaling pathway, or both signaling pathways, and wherein said mutant cells comprise an HSV thymidine kinase gene operatively linked to an IL-1 or TNF inducible promoter and a positive selection gene operatively linked to an IL-1 or TNF inducible promoter.

3. The method of claim 2 wherein said chemical mutagenizing agent induces frameshift mutations.

4. The method of claim 3 wherein said positive selection gene encodes a product that renders the transfected cell resistant to an antibiotic.

5. The method of claim 2 wherein the transfected cells and the mutagenized cells are selected in medium containing IL-1.

6. The method of claim 2 wherein the transfected cells and the mutagenized cells are selected in medium containing TNF.

7. A mutant cell made by the method of claim 2.

8. The mutant cell of claim 7, wherein the mutant cell is unresponsive to IL-1.

9. The mutant cell of claim 7, wherein the mutant cell is unresponsive to TNF.

* * * * *

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
        (A) LENGTH: 799 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:1:

```
GCCTGCCTCG GCCTCCCAAA GTGGTGGGAT TACAGGCATG AGCCACTGTG CCTGGCCTCC      60

TTTTTATTTT TTTCACTGAA CAAACCATGA AACTTTCCCA GATGTAAATA TCTATTTCCC     120

ATTTTTCTTT TTTTAAAATA AGGCATTATT TTAACCATTT GAGTGTTAGA TATTATTTTT     180

AGATAATATT TTAATTTAGC ATAACTGCCA TGCAAAATCT GAAGATTAAT ATCTACCTTG     240

TGAGTCATTC CTCTGTGAGA CAGTGCATGT TAAATATGTT GAATTGGCAG GTGAAAAAGG     300

AAGAAAAAAT GAGTAGTGAT TGGTTATCCA CAGCTATGAA TGAGAAATTG AAGGTAGTAG     360

ACTATGGATG ACAAACCTAT TCTTGGTTTC CTTCTGTTTC TGAAATTCTA ATTACTACCA     420

CAACTACATG AGAGACACTA CTAACAAGCA AAGTTTTACA ACTTTTTAAA GACATAGACT     480

TTATGTTATT ATAATTAAAA ATCATGCATT TTTGTCATAT TAATAAAATT GCATATACGA     540

TATAAAGGCA TGGACAAAGG TGAAGTAGCT TCAAGAGACA GAGTTTCTGA CATCATTGTA     600

ATTTTAAGCA TCGTGGATAT TCCCGGGAAA GGTTTTTGGA TGCCATTGGG GATTTCCTCT     660

TTACTGGATG TGGACAATAT CCTCCTATTA TTCACAGGAA GCAATCCCTC CTATAAAAGG     720

GCCTCAGCCA AAGTAGTGTT CAGCTGTTCT TGGCTGACTT CACATCAAAA CTCCTATACT     780

GACCTGAGAC AGAGGCAGC                                                  799
```

(2) INFORMATION FOR SEQ ID NO:2:

(i) SEQUENCE CHARACTERISTICS:
        (A) LENGTH: 12 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:2:

```
GGGGACTTTC CC                                                          12
```

-continued

```
(2) INFORMATION FOR SEQ ID NO:3:

(i) SEQUENCE CHARACTERISTICS:
        (A) LENGTH: 24 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:3:

GAGCAGAGGG AAATTCCGTA ACTT                                              24
```